(12) United States Patent
Norris

(10) Patent No.: US 6,720,734 B2
(45) Date of Patent: Apr. 13, 2004

(54) OXIMETER WITH NULLED OP-AMP CURRENT FEEDBACK

(75) Inventor: Mark A. Norris, Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/215,935

(22) Filed: Aug. 8, 2002

(65) Prior Publication Data

US 2004/0030231 A1 Feb. 12, 2004

(51) Int. Cl.[7] .............................................. H05B 37/02
(52) U.S. Cl. ...................... 315/149; 315/291; 315/307; 372/38.02; 600/323; 600/310; 356/41
(58) Field of Search ................................. 315/149, 291, 315/307, 169.3; 600/323, 310; 372/38.02, 38.07; 356/41

(56) References Cited

U.S. PATENT DOCUMENTS

| | | | | |
|---|---|---|---|---|
| 4,001,667 A | * | 1/1977 | Bober ........................... 356/41 |
| 4,504,776 A | * | 3/1985 | Haville ......................... 323/288 |
| 5,025,204 A | * | 6/1991 | Su ................................. 323/274 |
| 5,179,565 A | * | 1/1993 | Tsuchiya et al. ........... 372/38.06 |
| 6,097,159 A | * | 8/2000 | Mogi et al. .................. 315/151 |
| 6,510,168 B1 | * | 1/2003 | Kikuchi ..................... 372/38.02 |

* cited by examiner

Primary Examiner—James Clinger
Assistant Examiner—Ephrem Alemu
(74) Attorney, Agent, or Firm—Marsh Fischmann & Breyfogle LLP

(57) ABSTRACT

A method of producing a diode drive current in an oximeter includes sensing at least a part of a current passing through the diode and converting the sensed current to a sensed voltage, inputting the sensed voltage to a feedback amplifier for stabilizing the current passing through the diode, and eliminating an offset voltage across inputs of the feedback amplifier. A pulse oximeter includes a diode for emitting light flashes, a feedback amplifier having inputs, a feedback capacitor, and an output, the feedback amplifier stabilizing a current passing through the diode, a nulling amplifier having inputs, a nulling capacitor, and an output, the nulling amplifier charging and discharging the feedback capacitor until the inputs of the feedback amplifier are at a same voltage. The operation may include synchronizing an elimination of input offset voltages of the feedback and nulling amplifiers with on or off state of diode current.

26 Claims, 2 Drawing Sheets

OXIMETER WITH NULLED OP-AMP CURRENT FEEDBACK

BACKGROUND

1. Field of the Invention

The present invention relates generally to an apparatus' and method for improving stability in a current feedback circuit and, more particularly, to a method and apparatus for eliminating low-frequency drift in the diode drive circuit of an oximeter.

2. Related Work

A pulse oximeter is a type of blood gas monitor which non-invasively measures an amount of saturation of oxygen in the blood. The saturation of oxygenated blood may be determined from the peak-to-peak voltages or from instantaneous differential voltages for two plethysmographic waveforms measured at separate wavelengths. The two waveforms are produced by driving a visible red light-emitting diode (LED) and an infrared LED to produce two lights that pass through a patient's tissue, and then detecting the light on an opposite side or same side of the tissue using one or more photodetectors. The light-emitting LEDs are placed in a probe that is attached to the patient's body in a preferred location for the particular application. Although most conventional oximeters use the red and infra-red LEDs, other devices such as surface emitting laser devices having different wavelengths may also be used, and the number of LEDs can vary according to the specific measurement application. For example, it is known to set a number of laser diodes to be equal to or greater than the number of blood analytes that are to be measured by the instrument.

A conventional photodetector output signal indicates the attenuation of the two different wavelength lights from the LEDs after the lights pass through the patient's body. In order to obtain a degree of consistency and ease of use, the photodetector is generally placed in a clip or similar device attached to the patient's finger or earlobe. Attenuation of the lights is substantially constant except for the flow of blood. Thus, the constant attenuation due to the light passing through the patient's skin and other tissue can be determined and filtered from the photodetector signal, thereby obtaining a signal representing the desired blood oxygen characteristics. Signals containing a component related to a patient's pulse are known as plethysmographic waves and are used in blood gas saturation measurements. So, for example, the red/infra-red ratio for waveforms at different wavelengths may be analyzed to, obtain oxygenization values.

A photoplethysmographic measurement system used for oximetry typically isolates and separates components of composite detected signals in order to identify and remove noise sources, and then analyzes pulsatile components related to blood oxygen measurements. Conventional systems utilize complex signal processing for filtering noise and separating-out the signals that are due to absorption of the emitted diode light by the patient's tissue other than the arterial vessels. In oximetry detection and processing, it is critical to reduce noise because signal levels for measuring arterial blood oxygen saturation levels are extremely small. Ambient light can generate high levels of electrical noise unless detectors are shielded and adapted to physically blocking external light during a measurement. Other noise sources are typically present in, for example, a hospital environment. Electromagnetic radiation from various patient monitors may each have their own particular operating frequencies, a hospital may use radiotelemetry in systems such as wireless patient charts, and RF noise from cell phones, computers, and television, etc. may create a combined complex background noise that can combine and interfere with the ambient light noise. Similarly, patient motion causes motion artifacts that create difficulties in providing accurate oximetry measurements.

It is known to activate the red and infra-red LEDs during different time periods, where the two LEDs are cycled on and off alternately, in order to enable the photodetector to receive one signal at a time. As a result of generating LED pulse trains in a time-division manner, a composite time-division signal is then received by the photodetector. Alternatively, switching of LEDs may be related to other parameters such as maintaining a particular duty cycle without regard to time-division multiplexing (TDM). Various methods, not limited to TDM or to periodic switching, for modulating the LEDs can also be employed.

The term "noise" is known to those of ordinary skill in the oximetry art to include any signal portions relating to ambient light, motion artifacts, absorption variance, electromagnetic radiation, electrical interference, magnetic fields, electronic interference such as harmonics or RF, and others. However, conventional diode driver circuits have not been optimized for producing as clean a diode drive signal as possible. There are two general types of noise associated with an op-amp that are relevant to an LED drive circuit in an oximeter. "1/f noise" is noise which becomes greater per unit bandwidth as the frequency decreases, whereas "white noise" remains constant and flat over a broad range of frequencies.

In order to increase the accuracy and resolution of the oximeter, it is desirable to minimize noise in the circuitry used to produce one or more drive currents for causing the LEDs to illuminate. Conventional LED drive circuits have been designed to reduce photic noise generated by the LEDs, in order to maximize a signal-to-noise ratio for the arterial attenuation signal(s) used in processing oximetry data. However, the conventional circuits use ultra low noise operational amplifiers with high gain, which are expensive and inefficient, or simply ignore the problem of a noisy drive circuit because other parts of the oximetry measurement device dominate a system noise. The conventional systems use operational amplifiers that have an ultra low noise specification, which amounts to compensating for rather than eliminating a noise source. As is further discussed below, conventional oximetry systems were not able to see a problem of noise in the diode driver circuit because of conventional signal processing limitations.

Conventional diode drive current circuits may also use "chopper" type op-amp configurations that create additional noise when a corresponding LED is on, due to chopping that is not synchronous with the rest of the system.

Other conventional ways to address a noise problem in an oximeter include using filters to reduce the effects of ambient electromagnetic noise in electronic monitoring instruments, especially when the noise source frequency (or a harmonic of the noise source frequency) is approximately the same as the fundamental frequency or harmonics at which the instrument is operating. Another conventional example is a use of a static bandpass filter to remove a portion of the photodetector's output noise signal that is outside an identified bandwidth of interest, leaving random and/or erratic noise that is within the filter's passband. A processor has then been used to separate-out primary signal portions in order to isolate and identify the remaining noise signals, which are then removed using, for example, an adaptive noise canceller. Such a scheme is known as correlation canceling.

A method such as correlation canceling used in conventional oximeters simply accounts for various noise sources by identifying and isolating those separate noises in a processing of detected signals. However, such processing does not isolate, reduce, or eliminate a driver circuit noise itself.

Of particular interest for improving the oximeter performance is a problem of low frequency drift (0.5 to 10 Hz) in the LED drive circuitry and in the intensity level of the LEDs, which then creates drift in a detected signal, particularly in low perfusion conditions where the AC (measurement) component of the LED intensity is small. If the power and intensity of the LED varies within the physiologically-related passband ("physio passband"), the resultant intensity variation becomes an amplified error that is subsequently read as a phisiological signal by a detector, creating an erroneous oximeter reading.

SUMMARY OF THE INVENTION

Since a signal-to-noise ratio is increased by decreasing the noise, a decrease in the floor noise allows a lower limit for low-pass filtering within the diode drive circuit. The present invention is addressed to this object as well to generally eliminating low frequency drift in LED intensity. The present invention also has an object of improving detection of low level signals. The present invention also has an object of improving a low frequency noise elimination in an LED drive circuit. The present invention also has an object of improving control of noise generation in an LED drive circuit. For example, the problem of LED intensity variation within the physio passband of oximeter operation can be traced to such noise being generated by the LED drive circuit.

A method according to the present invention includes nulling an operational amplifier (op-amp) disposed in the feedback path of a diode drive circuit.

A method of producing a diode drive current in an oximeter, according to the present invention, can include sensing at least a part of a current passing through the diode and converting the sensed current to a sensed voltage, inputting the sensed voltage to a feedback amplifier for stabilizing the current passing through the diode, and eliminating an offset voltage across inputs of the feedback amplifier.

A pulse oximeter that converts pulses into light flashes, according to the present invention, can include a diode for emitting the light flashes, a feedback amplifier having inputs, a feedback capacitor, and an output, the feedback amplifier being operative to stabilize a current passing through the diode, a nulling amplifier having inputs, a nulling capacitor, and an output, the nulling amplifier being operative to charge and discharge the feedback capacitor until the inputs of the feedback amplifier are at a same voltage.

This summary does not limit the invention, which is instead defined by the appended claims.

BRIEF DESCRIPTION OF THE DRAWING FIGURE

DETAILED DESCRIPTION

In general, none of the prior art has considered any "noise" due to a diode current driving circuit. This is because the conventional signal processing for a detected oximetry signal was unable to detect, discern, or distinguish any noise as being due to the diode driving circuit. Conventional oximetry systems have not attempted to provide a "clean" LED drive circuit with expanded dynamic range, as in the present invention, because a typical detection signal processing did not have the highly increased resolution provided by, for example, state-of-the art oversampling hardware. With better processing hardware having recently been developed, a resultant higher processing capability and greater resolution allows "seeing" smaller noises that were previously unnoticed. Along with improved resolution, it is of paramount importance to reduce noise sources in the LED drive circuitry of an oximeter rather than separating-out resultant signals during processing of signals from the oximeter's photodetector. By using as clean a diode driving circuit as possible, less noise is present in downstream signals.

Since a signal-to-noise ratio is increased by decreasing the noise, a decrease in the floor noise-allows a lower limit for low-pass filtering within the diode drive circuit. The present invention is addressed to this object as well to generally eliminating low frequency drift in LED intensity. Low frequency drift (0.5 to 10 Hz) in the intensity of the LEDs creates a resultant drift in an oximeter measurement, particularly in low perfusion conditions where the AC component of the LED intensity is small. A related application by the present inventor, "Feedback Controlled LED Switching," details how to use a constant reference voltage to obtain a low noise. However, a problem of 1/f noise in the feedback operational amplifier limits the reduction in low frequency drift.

Various noises-such as those due to ambient light can create a DC offset for an input to the operational amplifier used as a current feedback circuit in an LED current driver. The present invention has an object of removing such an offset, whereas conventional systems merely indirectly compensate for such an offset.

Figure 1:
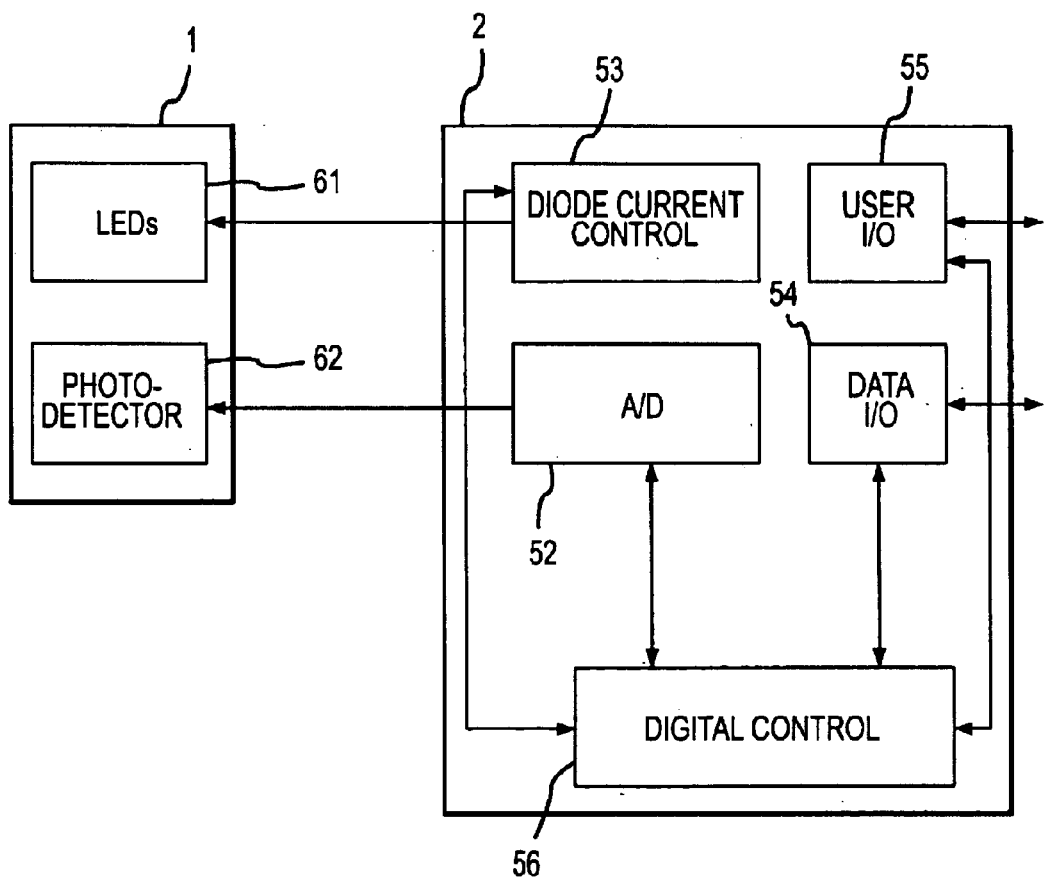
FIG. 1 is a highly schematic diagram of a conventional pulse oximeter system.

FIG. 1 shows the basic elements of an exemplary pulse oximeter used for implementing the disclosed embodiments. A probe 1 is affixed to a patient to be monitored. The probe 1 contains LEDs 61 that illuminate when a current passes through them, and a photodetector 62 for detecting light. The light emitted by the LEDs 61 passes through the patient's tissue and a portion of the emitted light is detected by at least one photodetector 62 that is placed on a same or a different location on the patient. The detected light can, therefore, be in a direct path of the emitted light, or can detect reflected light. A monitor 2 contains a user input/output section 55 that may include a speaker, keypad, and display device which allow a user to operate the pulse oximeter. For example, a user is able to adjust a measurement period and/or measurement cycle parameters, and see and hear measurement data and operational status. A digital control section 56 controls the internal operations of the oximeter. A diode current driver circuit 53 controls a current being supplied to individual LEDs 61. An analog-to-digital (A/D) converter 52 receives detection signals from the photodetector 62, converts those detected signals to digital signals that are then processed by the digital control section 56. The monitor 2 also contains a data input/output section 54 that provides both a serial digital data output and an analog output, which allow the oximeter to interface with external equipment, such as a computer. The data input/output section 54 also accepts control signals from external equipment in order to remotely change or control operation of the oximeter.

Figure 2:
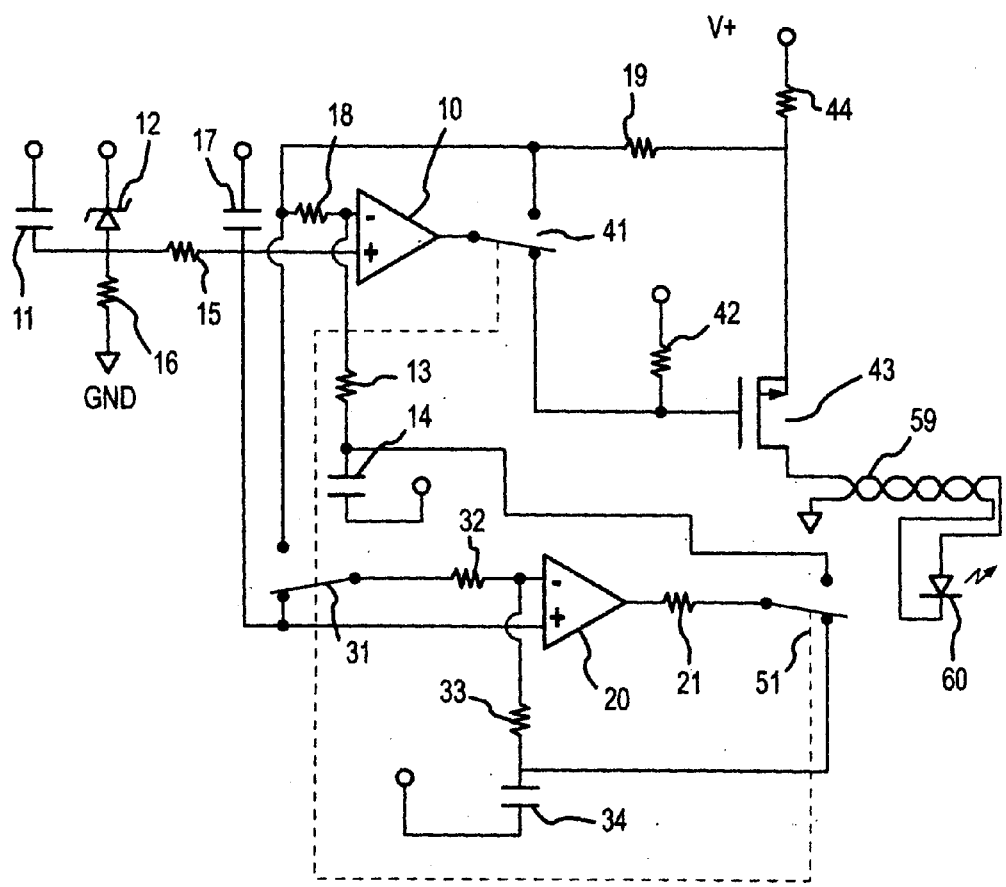
FIG. 2 is a schematic diagram of a nulling op-amp current feedback circuit according to an embodiment of the present invention.

FIG. 2 shows an exemplary embodiment of a nulling op-amp current feedback circuit for driving an LED of an oximeter. In FIG. 2, a current feedback amplifier 10 and a nulling amplifier 20 each have their non-inverting inputs connected to a reference voltage $V_{REF}$ through a resistor 15. The other end of resistor 15 is tied to the supply voltage via capacitor 11. The reference voltage $V_{REF}$ is maintained at a fixed level by operation of a zener diode 12. The zener diode 12 has one end connected to a positive supply voltage V+, and the other end connected to one end of a resistor 16. The other end of resistor 16 is connected to ground. A reference voltage $V_{REF}$ terminal A is thereby located at the non-inverting input of the current feedback amplifier 10. A capacitor 17 is connected between the positive supply voltage V+ and $V_{REF}$ terminal A. A first SPDT switch 31 has one throw terminal connected both to $V_{REF}$ terminal A and to the non inverting input of a nulling amplifier 20. The other throw terminal of switch 31 is connected to the non-inverting input of current feedback amplifier 10 through a resistor 18, to a throw terminal of a second SPDT switch 41, and to one end of a resistor 19. The common pole of switch 31 is connected to one end of resistor 32. The other end of resistor 32 is connected to the inverting input of the nulling amplifier 20 and to one end of resistor 33. The other end of resistor 33 is connected to a throw terminal of a third SPDT switch 51, and to one end of a nulling capacitor 34. The other end of the nulling capacitor 34 is connected to the supply voltage V+. The inverting input of current feedback amplifier 10 is also connected to one end of resistor 13. The other end of resistor 13 is connected to the other throw terminal of switch 51 and to one end of feedback nulling capacitor 14. The other end of capacitor 14 is connected to the supply voltage V+. The output of current feedback amplifier 10 is connected to the common pole of switch 41. The output of nulling amplifier 20 is connected to the common pole of switch 51 via nulling slew resistor 21. The other throw terminal of switch 41 is connected to the supply voltage V+ via pullup resistor 42 and to the gate of transistor 43. The source of transistor 43 is connected to the other end of resistor 19 and is also connected to the supply voltage V+ via a current sense resistor 44. The drain of transistor 43 is connected to the anode of diode 60 through a cable 59. The cathode of diode 60 is connected to ground via the cable 59. In order to prevent any possible oscillation current (ringing noise) caused, for example, when the cable 59 is long and a diode switching speed is high, the output current driving portion may be modified to prevent any oscillations, for example, as disclosed in co-pending application Ser. No. 10/215,904, entitled "Ferrite Stabilized LED Drive," incorporated herein by reference.

In the FIG. 2 embodiment, switches 31, 41, 51 are configured as three ganged SPDT switches. Other switch combinations that implement a triple ganged switching arrangement can also be used, such as a use of a DPDT together with a SPDT. In a preferred embodiment, the transistor 43 is a FDC6506P dual P-channel logic level powertrench MOSFET available from Fairchild, although any suitable transistor may be used. Although a zener diode type circuit is used as a reference voltage source in the FIG. 2 embodiment, other reference voltage sources may be used, such as precision low noise reference voltage sources. The reference voltage $V_{REF}$ is a set-point voltage that the current feedback amplifier 10 is attempting to stabilize across the current sense resistor 44. The current sense resistor 44 converts a current, which corresponds to the current through the diode 60, to the voltage that is being stabilized by the current feedback amplifier 10.

The switches 31, 41, 51 are shown in the ON position in FIG. 2. During an ON cycle, the nulling amplifier 20 charges and discharges the nulling capacitor 34. This acts to eliminate any effective input offset voltage in the nulling amplifier 20. The input offset voltage is thereby reduced by a factor of 1/(gain of the amplifier), which is a significant amount. It would be readily apparent to one skilled in the art that a selection of an ON position for the switches 31, 41, 51 is arbitrary and that, for example, the nulling amplifier 20 may be operated 180 degrees out of phase with respect to the described operation of the feedback amplifier 10. Other variations of the described embodiments are envisaged, such as a use of multiple feedback paths.

When the switches 31, 41, 51 switch to an OFF position, the nulling amplifier 20 charges and discharges the feedback nulling capacitor 14 until both inputs of the feedback amplifier 10 are at exactly the same level, i.e., the feedback amplifier 10 has no offset. Ganged switches 31, 41, 51 provide synchronizing of the chargings and dischargings of capacitors 14, 34 with a turning on and off of the current passing through the diode. The synchronizing in FIG. 2 effects alternate eliminating of respective offset voltages across the input terminals of the feedback amplifier and nulling amplifier.

Isolation resistors 18, 19, and 32 and nulling capacitors 14, 34 are each chosen to be large enough so that the nulling capacitors 14, 34 do not substantially charge or discharge when actively nulling respective amplifiers. Preferably, the nulling capacitors 14, 34 never charge or discharge except when an adjustment is being made by the nulling amplifier 20. The isolation resistors 18, 19, 32 must, however, be small enough values so that they do not add substantial noise to the circuit, or cause input offset and bias currents that would create large offsets.

The nulling slew resistor 21 limits how fast the nulling amplifier 20 can change the voltage of the nulling capacitor 34, in order to add stability to the nulling amplifier 20. The effective slew rate must be substantially greater than the highest frequency to be nulled. For example, a highest frequency rate to be nulled in an exemplary oximeter can be 1.0, 10, or 50 Hz. Charge injection created by the switches 31, 41, 51 is a potential problem that must be considered for the FIG. 2 embodiment. However, because such a charge injection does not vary appreciably, a slight fixed DC offset has been shown to be well within an acceptable range for oximetry applications. Moreover, the actions of amplifiers 10, 20 tend to drive-out noise generated by the switches 31, 41, 51.

Since the nulling op-amp current feedback circuit of the present invention can be implemented using inexpensive low-power operational amplifiers, it may be formed in a package such as an application specific integrated circuit (ASIC). An exemplary maximum power consumption for an operational amplifier of a nulling op-amp current feedback circuit is 2 mA, which can easily be implemented in the ASIC device.

The diode driver circuit of FIG. 2 can also include a delay circuit (not shown), that provides a delay in the charging and discharging of capacitor 34 for a predetermined period after a time when the diode begins an on state. One example of such a use is for optimizing a timing of the nulling circuit to account for various time constants and inherent delays in the operation of constituent circuit elements.

Low-frequency noise is of particular interest in the reference voltage of a diode current drive circuit op-amp used in oximetry applications. Reference voltages always have some inherent noise, and by being more adaptable to low-pass filtering, the reference voltage is made less noisy. As a result of the invention of co-pending application Ser. No. 10/215,878, "Feedback-controlled LED Switching," incorporated herein by reference, when the reference voltage is not switched, a reference voltage source can be used that has a very small bandwidth, and an extremely large amount of low-pass filtering that eliminates all low-frequency noise effects, including harmonics of corresponding low-frequency noise (e.g., eliminating any effects from a patient heartbeat, even below 30 beats per minute (0.5 Hz) and above 250 beats per minute). In order to have as little noise as possible in a frequency band of interest, by not switching the reference, the bandwidth of the reference can be very low (e.g., 0.2 to 0.3 Hz), well below the 0.5 Hz absolute minimum heartbeat-related noise, for a demodulated signal. As a result of direct connection of the reference voltage to the op-amp 10 (without using an intervening switch), the low-pass filtering removes any noise on the constant reference voltage because the requirements for a reference voltage source are much less than with conventional devices. By not directly switching the reference voltage, the reference voltage signal is much cleaner compared with conventional diode driving circuits. By placing the respective switch for a diode within the feedback portion of the driving circuit, any noise being injected by the switch is driven out by the op-amp's feedback loop. In other words, an op-amp cannot get rid of noise from a reference voltage being applied to its non-inverting input, whereas by changing the generation location for noise generated by a switching of the reference voltage to be within the feedback loop of the op-amp, the switching noise is driven out by the cancellation action of the feedback. It is understood by one skilled in the art that the 'elimination' of the offset voltages of the feedback amplifier and of the nulling amplifier is relative to the actual effect on the respective amplifiers. The charging and discharging of the capacitors for each amplifier essentially reduces a corresponding input offset voltage by a factor of 1/(gain of the op-amp), which is significant.

Although the present invention has been described in conjunction with a preferred embodiment, it is to be understood that modifications and variations may be made without departing from the spirit and scope of the invention as understood by those skilled in the art. Such modifications and variations are considered to be within the purview and scope of the invention as defined by the appended claims.

What is claimed is:

1. A method of producing a diode drive current in an oximeter, comprising:
   sensing at least a part of a current passing through the diode and converting the sensed current to sensed voltage;
   inputting the sensed voltage to a feedback amplifier for stabilizing the current passing through the diode; and
   eliminating an offset voltage across inputs of the feedback amplifier by charging and discharging a first capacitor connected to one of the inputs of the feedback amplifier.

2. A method according to claim 1, further comprising synchronizing the charging and discharging of the first capacitor with a turning on and off of the current passing through the diode.

3. A method according to claim 1, wherein the charging and discharging of the first capacitor is performed during a period when the diode is in an off state.

4. A method according to claim 3, further comprising eliminating an input offset voltage of a nulling amplifier when the diode is in an on state.

5. A method according to claim 1, wherein the charging and discharging of the first capacitor is performed by a nulling amplifier.

6. A method according to claim 5, further comprising maintaining an effective slew rate for the nulling amplifier that is substantially greater than a highest frequency to be nulled.

7. A method according to claim 5, further comprising the nulling amplifier charging and discharging a second capacitor connected to an input of the nulling amplifier.

8. A method according to claim 7, wherein the charging and discharging of the second capacitor is performed during a period when the diode is in an on state.

9. A method according to claim 7, further comprising delaying a performing of the charging and discharging of the second capacitor for a predetermined period after a time when the diode begins an on state.

10. A method according to claim 7, further comprising limiting how fast the nulling amplifier can change a voltage across the second capacitor.

11. A method according to claim 7, further comprising synchronizing the charging and discharging of the second capacitor with a turning on and off of the current passing through the diode.

12. A method according to claim 7, further comprising synchronizing the chargings and dischargings of the first and second capacitors with a turning on and off of the current passing through the diode.

13. A method according to claim 12, wherein the synchronizing effects alternate eliminating, of respective offset voltages across the input terminals of the feedback amplifier and nulling amplifier.

14. A pulse oximeter that converts pulses into light flashes, comprising:
   a diode for emitting the light flashes;
   a feedback amplifier having inputs, a feedback capacitor, and an output, the feedback amplifier being operative to stabilize a current passing through the diode; and
   a nulling amplifier having inputs, a nulling capacitor, and an output, the nulling amplifier being operative to charge and discharge the feedback capacitor until the inputs of the feedback amplifier are at a same voltage.

15. A pulse oximeter as claimed in claim 14, wherein the diode is an LED.

16. A pulse oximeter as claimed in claim 14, wherein the diode is a laser diode.

17. A pulse oximeter according to claim 14, further comprising a current sense resistor for sensing at least a part of the current passing through the diode, wherein the stabilizing by the feedback amplifier is based on the current sensed by the current sense resistor.

18. A pulse oximeter as claimed in claim 14, further comprising a second switch operative to connect an output of the feedback amplifier to the feedback capacitor for performing the charging and discharging of the feedback capacitor.

19. A pulse oximeter as claimed in claim 14, further comprising a resistor operative to maintain an effective slew rate for the nulling amplifier that is substantially greater than a highest frequency to be nulled.

20. A pulse oximeter as claimed in claim 14, further comprising a limiter operative to limit a rate at which the nulling amplifier can change a voltage across the nulling capacitor.

21. A pulse oximeter as claimed in claim 14, further comprising a ganged switching arrangement synchronized with a turning on and off of the current passing through the diode, the switching arrangement being operative to alternately eliminate respective offset voltages across the inputs of the feedback amplifier and the nulling amplifier.

22. A pulse oximeter as claimed in claim 21, further comprising a transistor that is operative to turn the current through the diode on or off, wherein the ganged switching arrangement is further operative to control the turning on or off of the diode.

23. A pulse oximeter as claimed in claim 14, further comprising a first switch operative to connect the output of the nulling amplifier to the feedback capacitor for performing the charging and discharging of the feedback capacitor.

24. A pulse oximeter as claimed in claim 23, wherein the first switch is further operative to connect the output of the nulling amplifier to the nulling capacitor for charging and discharging the nulling capacitor until inputs of the nulling amplifier are at a same voltage.

25. A pulse oximeter as claimed in claim 23, wherein the operation of the first switch is synchronized with a turning on and off of the current passing through the diode.

26. A pulse oximeter as claimed in claim 23, further comprising a delay circuit operative to delay the charging and discharging of the second capacitor for a predetermined period after a time when the diode begins an on state.

* * * * *

UNITED STATES PATENT AND TRADEMARK OFFICE
CERTIFICATE OF CORRECTION

PATENT NO. : 6,720,734 B2
DATED : April 13, 2004
INVENTOR(S) : Norris

It is certified that error appears in the above-identified patent and that said Letters Patent is hereby corrected as shown below:

<u>Column 8,</u>
Line 45, after the word "voltage", insert -- level --.

Signed and Sealed this

Twenty-first Day of December, 2004

JON W. DUDAS
*Director of the United States Patent and Trademark Office*